(12) United States Patent
Kovalsky et al.

(10) Patent No.: US 10,869,757 B2
(45) Date of Patent: *Dec. 22, 2020

(54) VALVE PROSTHESIS AND METHOD FOR DELIVERY

(71) Applicant: Medtronic, Inc., Minneapolis, MN (US)

(72) Inventors: Igor Kovalsky, Minnetonka, MN (US); Jason Quill, Forest Lake, MN (US); Daniel Glozman, Metanya (IL); Ilia Hariton, Netanya (IL); Yossi Tuval, Even Yehuda (IL); Nadav Yellin, Irvine, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/831,588

(22) Filed: Dec. 5, 2017

(65) Prior Publication Data

US 2018/0110620 A1    Apr. 26, 2018

Related U.S. Application Data

(60) Continuation of application No. 14/962,824, filed on Dec. 8, 2015, now Pat. No. 9,867,698, which is a
(Continued)

(51) Int. Cl.
*A61F 2/24* (2006.01)

(52) U.S. Cl.
CPC .......... *A61F 2/2418* (2013.01); *A61F 2/2412* (2013.01); *A61F 2230/001* (2013.01);
(Continued)

(58) Field of Classification Search
CPC . A61F 2/2412; A61F 2/2418; A61F 2230/001
See application file for complete search history.

(56) References Cited

U.S. PATENT DOCUMENTS

| 5,545,215 A | 8/1996 | Duran |
| 6,458,153 B1 | 10/2002 | Bailey |

(Continued)

FOREIGN PATENT DOCUMENTS

| CN | 101172055 | 5/2008 |
| CN | 101754729 A | 6/2010 |

(Continued)

OTHER PUBLICATIONS

Third Office Action issued in CN Application No. 201480004193.6 by the China State Intellectual Property Office, dated Jun. 14, 2017.
(Continued)

*Primary Examiner* — Brian A Dukert
(74) *Attorney, Agent, or Firm* — Medler Ferro Woodhouse & Mills PLLC

(57) ABSTRACT

In some embodiments, a valve prosthesis includes an inlet portion that is substantially s-shaped and configured to engage the floor of the outflow tract of the native heart atrium. In some embodiments, a valve prosthesis includes a chordae guiding element configured to reduce bending of the chordae to reduce stress on the chordae during the cardiac cycle. In some embodiments, a valve prosthesis includes a central portion having an hourglass shape configured to pinch a native annulus in order to provide axial fixation of the valve prosthesis within a valve site. In some embodiments, a valve prosthesis includes a frame having an outflow end that is flared to provide a gap between an outflow end of the frame and an outflow end of prosthetic leaflets when the prosthetic leaflets are fully opened.

20 Claims, 19 Drawing Sheets

Related U.S. Application Data division of application No. 13/736,460, filed on Jan. 8, 2013, now Pat. No. 9,232,995.

(52) U.S. Cl.
CPC ... *A61F 2230/005* (2013.01); *A61F 2230/008* (2013.01); *A61F 2230/0054* (2013.01); *A61F 2230/0078* (2013.01)

(56) References Cited

U.S. PATENT DOCUMENTS

| | | |
|---|---|---|
| 7,101,396 B2 | 9/2006 | Artof et al. |
| 7,399,315 B2 | 7/2008 | Iobbi |
| 7,780,725 B2 | 8/2010 | Haug et al. |
| 8,449,599 B2 | 5/2013 | Chau et al. |
| 8,801,776 B2 | 8/2014 | House et al. |
| 10,182,907 B2 | 1/2019 | Lapeyre |
| 2004/0210304 A1 | 10/2004 | Sequin et al. |
| 2006/0020333 A1 | 1/2006 | Lashinski et al. |
| 2008/0071361 A1 | 3/2008 | Tuval et al. |
| 2010/0036479 A1 | 2/2010 | Hill et al. |
| 2010/0094411 A1 | 4/2010 | Tuval et al. |
| 2010/0268332 A1 | 10/2010 | Tuval et al. |
| 2011/0137397 A1* | 6/2011 | Chau ............ A61F 2/2418 623/1.11 |
| 2011/0208298 A1 | 8/2011 | Tuval et al. |
| 2012/0022640 A1 | 1/2012 | Gross et al. |
| 2012/0165928 A1 | 6/2012 | Nitzan et al. |
| 2014/0067054 A1 | 3/2014 | Chau et al. |

FOREIGN PATENT DOCUMENTS

| | | |
|---|---|---|
| CN | 101951858 A | 1/2011 |
| CN | 102639179 | 8/2012 |
| DE | 102006052564 | 12/2007 |
| WO | 2005/062980 A2 | 7/2005 |
| WO | 2008/097589 A1 | 8/2008 |
| WO | 2009/108615 A1 | 9/2009 |
| WO | WO2011/057087 | 5/2011 |
| WO | 2011/106137 A1 | 9/2011 |
| WO | 2011/106533 A1 | 9/2011 |
| WO | 2011/143263 A | 11/2011 |
| WO | 2012/030598 A2 | 3/2012 |
| WO | WO2012/061809 | 5/2012 |
| WO | 2012/085913 A2 | 6/2012 |
| WO | WO2012/095159 | 7/2012 |
| WO | WO2012/177942 | 12/2012 |
| WO | 2013/021374 A2 | 2/2013 |
| WO | 2013/059747 A1 | 4/2013 |
| WO | WO2013/072496 | 5/2013 |
| WO | 2013/086413 A1 | 6/2013 |
| WO | 2013/155970 A1 | 10/2013 |
| WO | 2013/175468 A2 | 11/2013 |
| WO | 2013/177684 A1 | 12/2013 |
| WO | 2014/121275 A1 | 8/2014 |
| WO | 2015/061378 A1 | 4/2015 |

OTHER PUBLICATIONS

Communication pursuant to Article 94(3) EPC issued in European Application No. 14701853.5, dated Nov. 26, 2018.
Notice on the First Office Action issued in Chinese Application No. 201810162292.7, dated Apr. 28, 2019.
Notification of the First Office Action issued in Chinese Application No. 201810159579.4, dated Jun. 14, 2019.
CN Application No. 201810159442.9, Chinese Notice of Second Office Action, dated Nov. 21, 2019, 12pgs.

\* cited by examiner

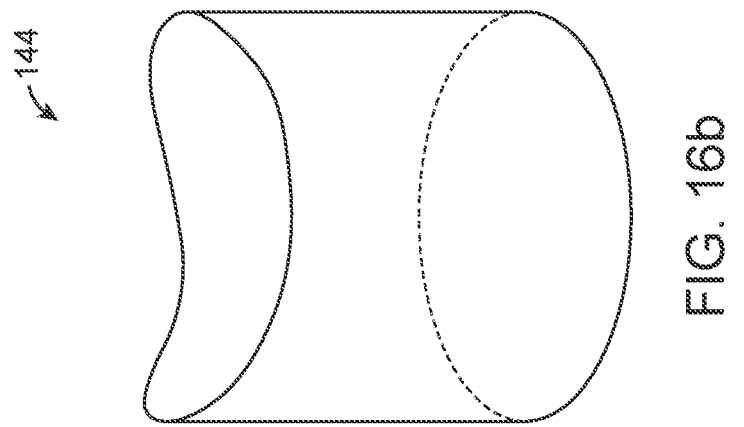
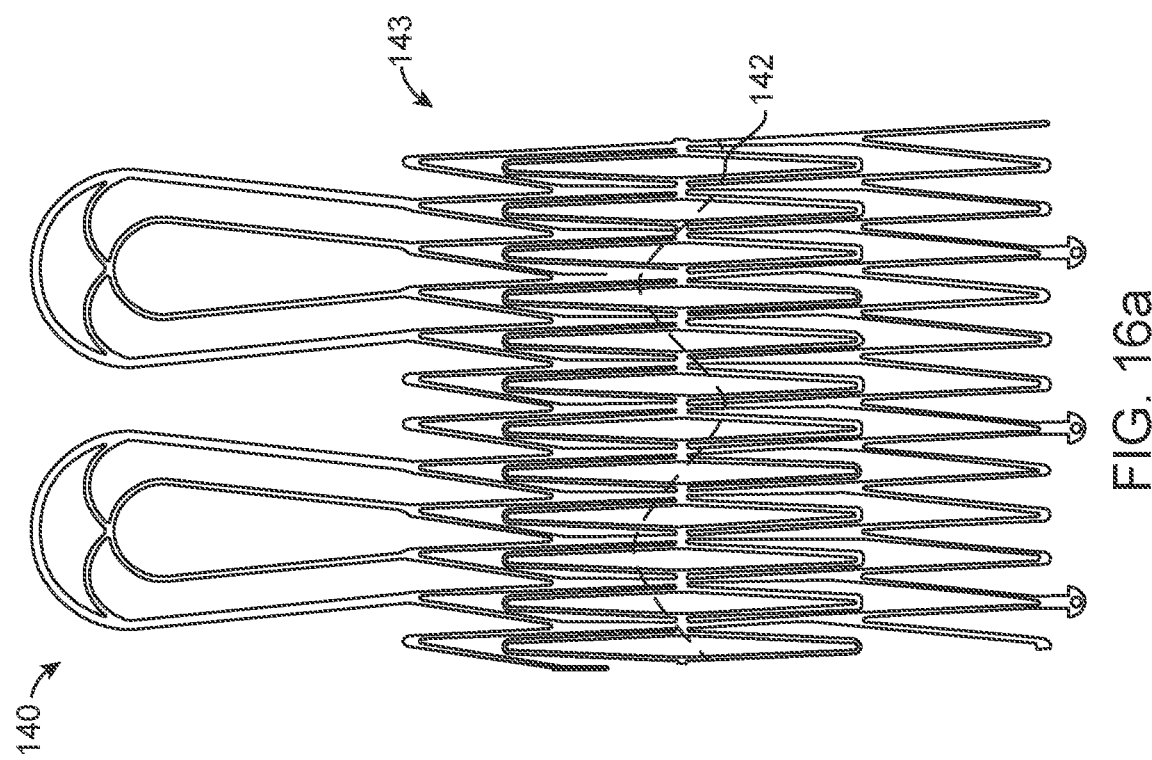
FIG. 16b
FIG. 16a

VALVE PROSTHESIS AND METHOD FOR DELIVERY

CROSS-REFERENCE TO RELATED APPLICATIONS

This application is a continuation of prior application Ser. No. 14/962,824, filed Dec. 8, 2015, now U.S. Pat. No. 9,867,698, which is a divisional of application Ser. No. 13/736,460, filed Jan. 8, 2013, now U.S. Pat. No. 9,232,995. The disclosures of which are incorporated by reference herein in their entirety.

BACKGROUND

Field

Certain embodiments of the present invention are related to artificial heart valve prostheses, frames, and methods of delivery thereof.

Background Art

Diseased or otherwise deficient cardiac valves can exhibit pathologies such as regurgitation and stenosis. Such valves can be repaired or replaced with prosthetic heart valves using a variety of techniques. For example, an open-heart surgical procedure can be conducted during which the heart can be stopped while blood flow is controlled by a heart-lung bypass machine. Alternatively, a minimally invasive percutaneous technique can be used to repair or replace a cardiac valve. For example, in some percutaneous techniques, a valve assembly can be compressed and loaded into a delivery device, which is then passed through a body lumen of the patient to be delivered to the valve site. There is a continuous need for improved valve prostheses for use in such techniques.

BRIEF SUMMARY

In some embodiments, a valve prosthesis for implantation into a native cardiac valve site of an individual can include a valve body and a frame supporting the valve body. The frame can include an inlet portion configured to engage the floor of the outflow tract of the native heart atrium and restrict movement of the valve prosthesis in a downstream direction of blood flow at the valve site. In some embodiments, the inlet portion can be substantially s-shaped.

In some embodiments, a valve prosthesis includes a valve body and a frame supporting the valve body. The frame can include a central portion configured to fit securely within an annulus of the valve site, a support arm extending from the central portion and configured to extend over and secure a native valve leaflet, and a chordae guiding element extending from the support arm and configured to engage chordae of the valve site. The chordae guiding element can be configured to angle the chordae so that the chordae are stretched to restrict movement of the valve prosthesis in an upstream direction of blood flow at the valve site. The chordae guiding element can be configured to reduce bending of the chordae to reduce stress on the chordae during the cardiac cycle.

In some embodiments, a valve prosthesis can include a valve body and a frame supporting the valve body. The frame can include a central portion configured to fit securely within an annulus of the native valve site. The central portion can have an hourglass shape configured to pinch the annulus in order to provide axial fixation of the valve prosthesis within the valve site.

In some embodiments, a valve prosthesis can include a valve body including prosthetic leaflets and a frame secured to the valve body. The frame can include an inlet portion configured to engage the floor of an outflow tract of the native heart atrium and restrict movement of the frame in a downstream direction of blood flow at the valve site. The frame can also include a central portion connected to the inlet portion and configured to fit securely within the native valve annulus. Portions of the outflow end of the frame can be flared to provide a gap between an outflow end of the frame and an outflow end of the prosthetic leaflets when the prosthetic leaflets are fully opened.

BRIEF DESCRIPTION OF THE DRAWINGS/FIGURES

The accompanying figures, which are incorporated herein, form part of the specification and illustrate embodiments of a valve prosthesis frame and delivery system. Together with the description, the figures further serve to explain the principles of and to enable a person skilled in the relevant art(s) to make, use, and implant the valve prosthesis described herein.

Figure 3:
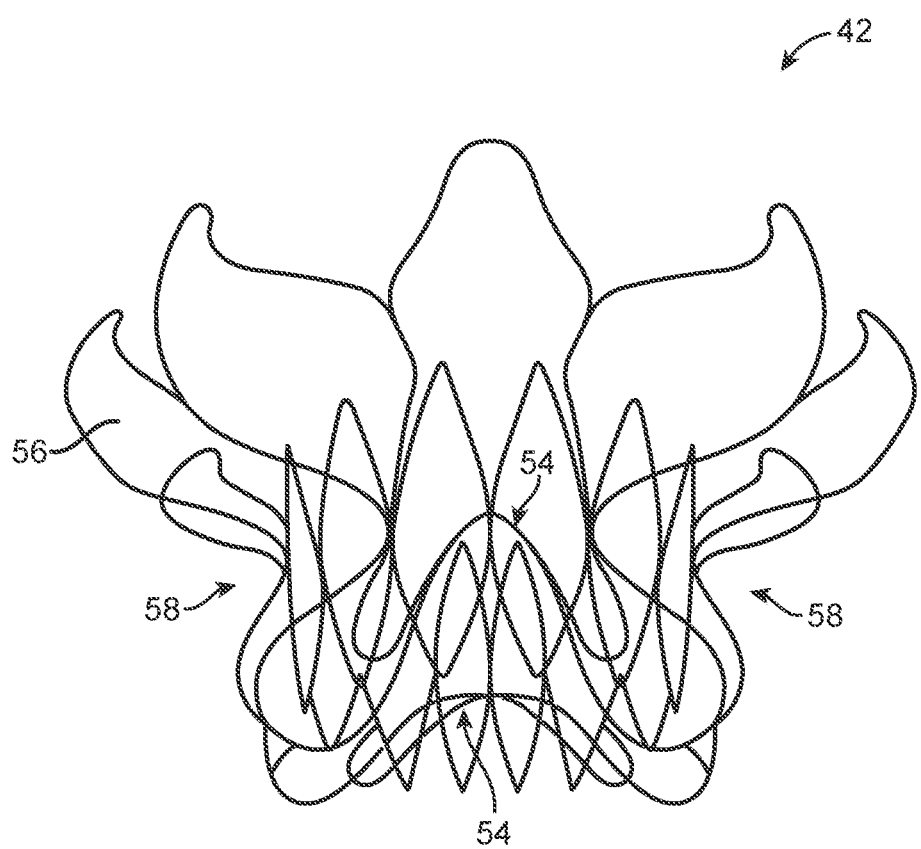
FIG. 3 illustrates a front view of a frame in accordance with an embodiment.

FIGS. 4a-b illustrate views of the frame of FIG. 3 implanted in a native mitral valve site.

Figure 5:
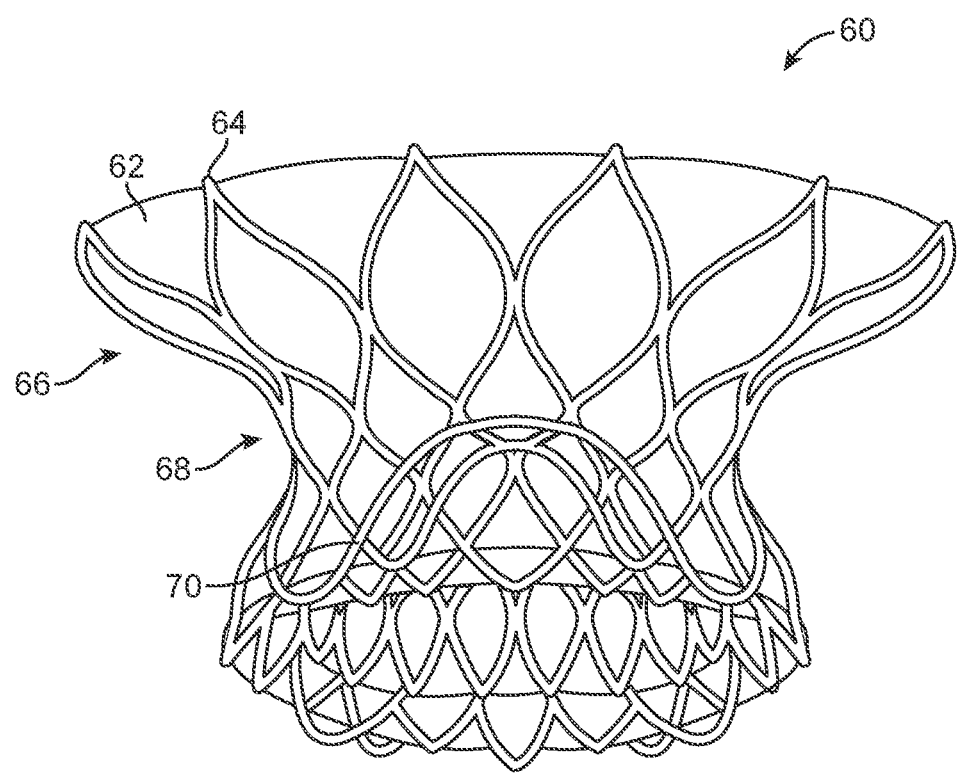

FIG. 5 illustrates a front view of a valve prosthesis in accordance with an embodiment.

Figure 6:
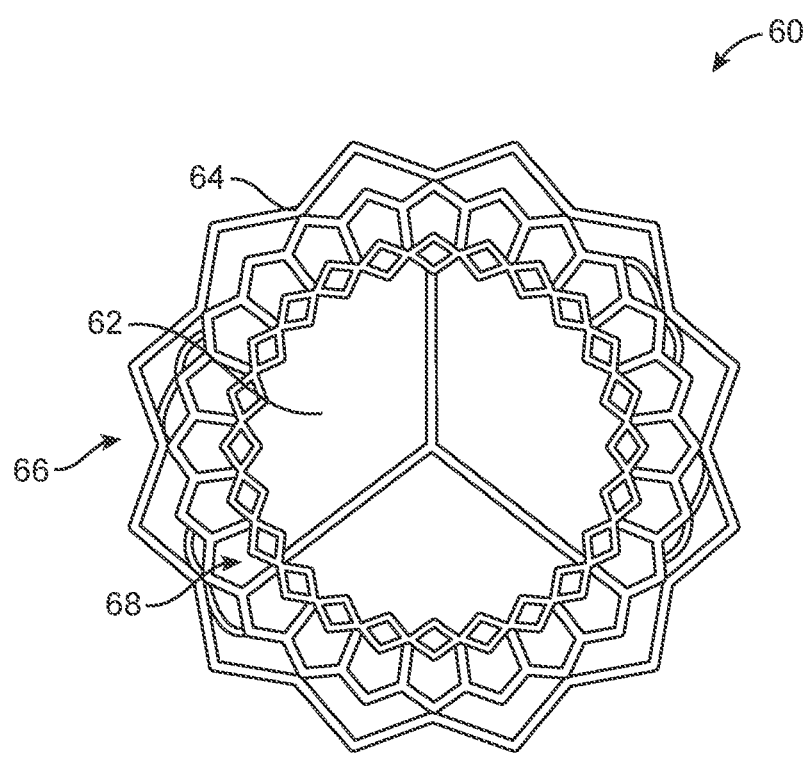

FIG. 6 illustrates a top view of the valve prosthesis of FIG. 5.

Figure 7:
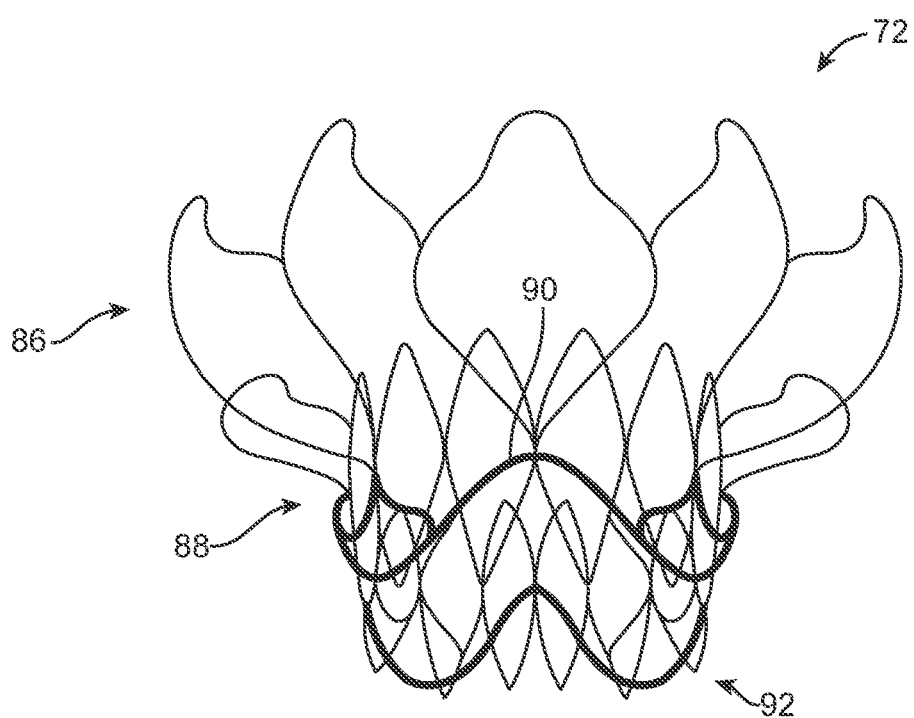

FIG. 7 illustrates a front view of a valve prosthesis in accordance with an embodiment.

Figure 8:
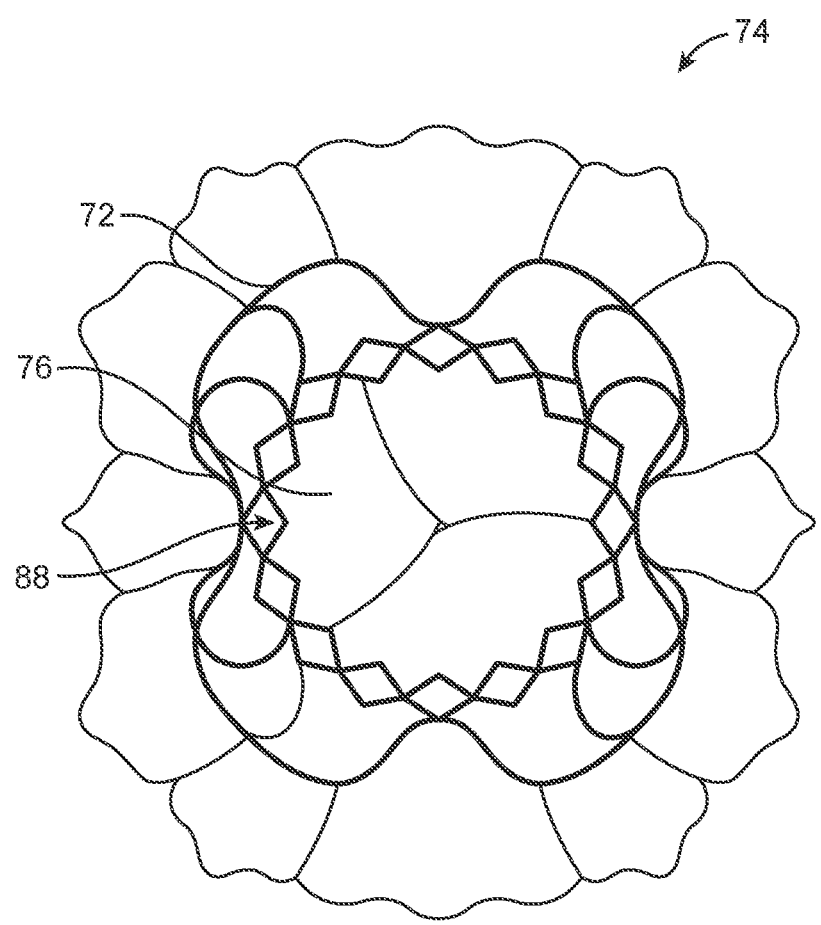

FIG. 8 illustrates a top view of the valve prosthesis of FIG. 7.

Figure 9B:
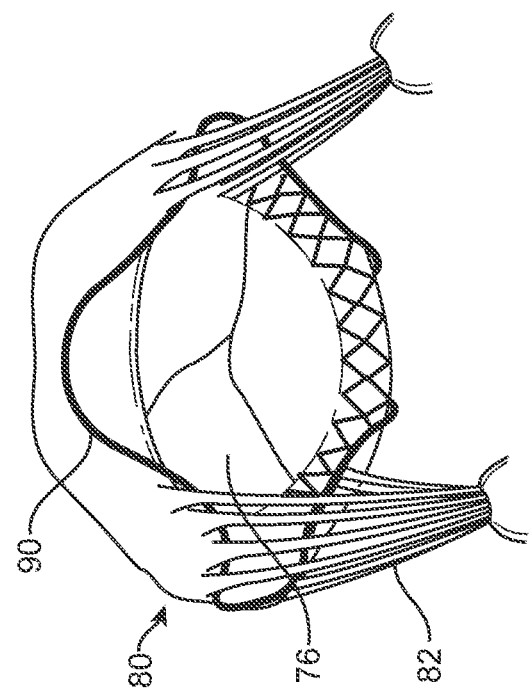
Figure 9A:
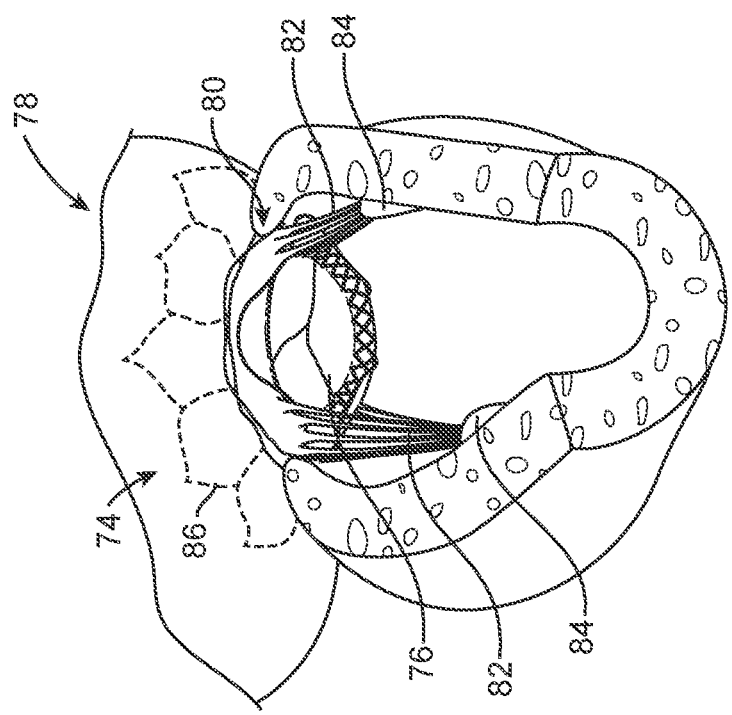

FIGS. 9a-b illustrate views of the valve prosthesis of FIG. 7 implanted in a native valve site.

Figure 10:
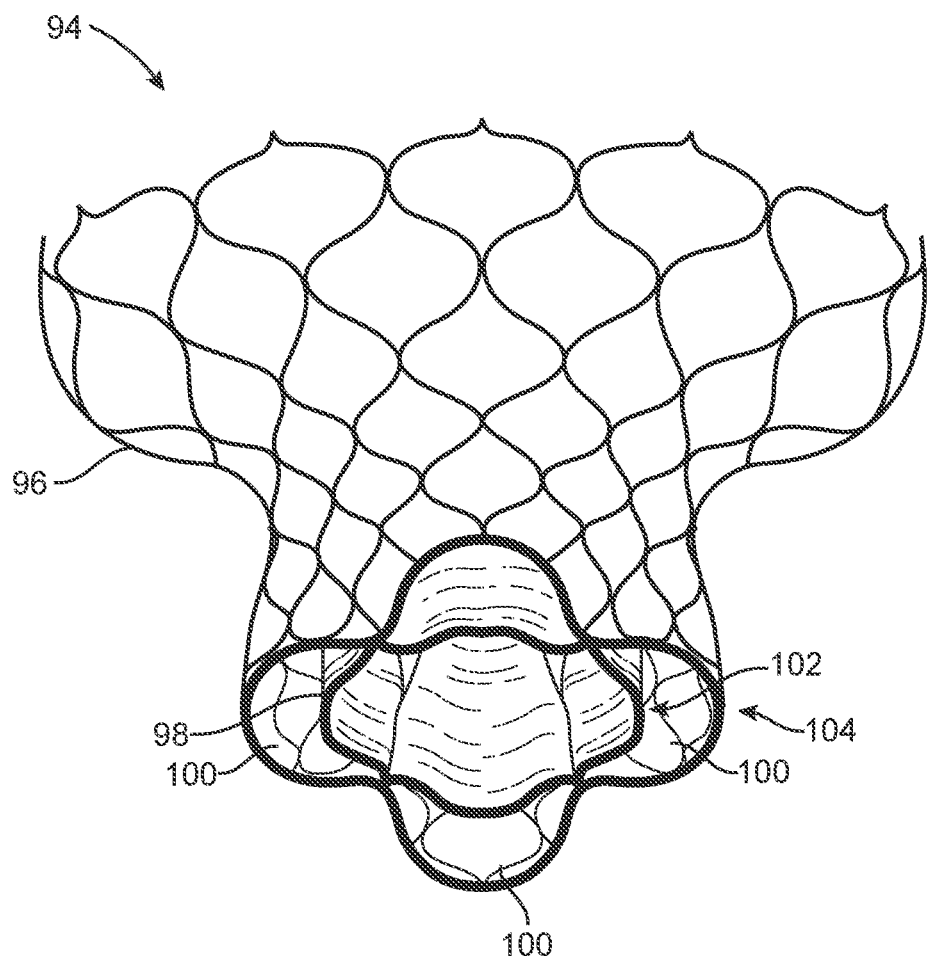

FIG. 10 illustrates a bottom-front perspective view of a valve prosthesis in an open position in accordance with an embodiment.

Figure 11:
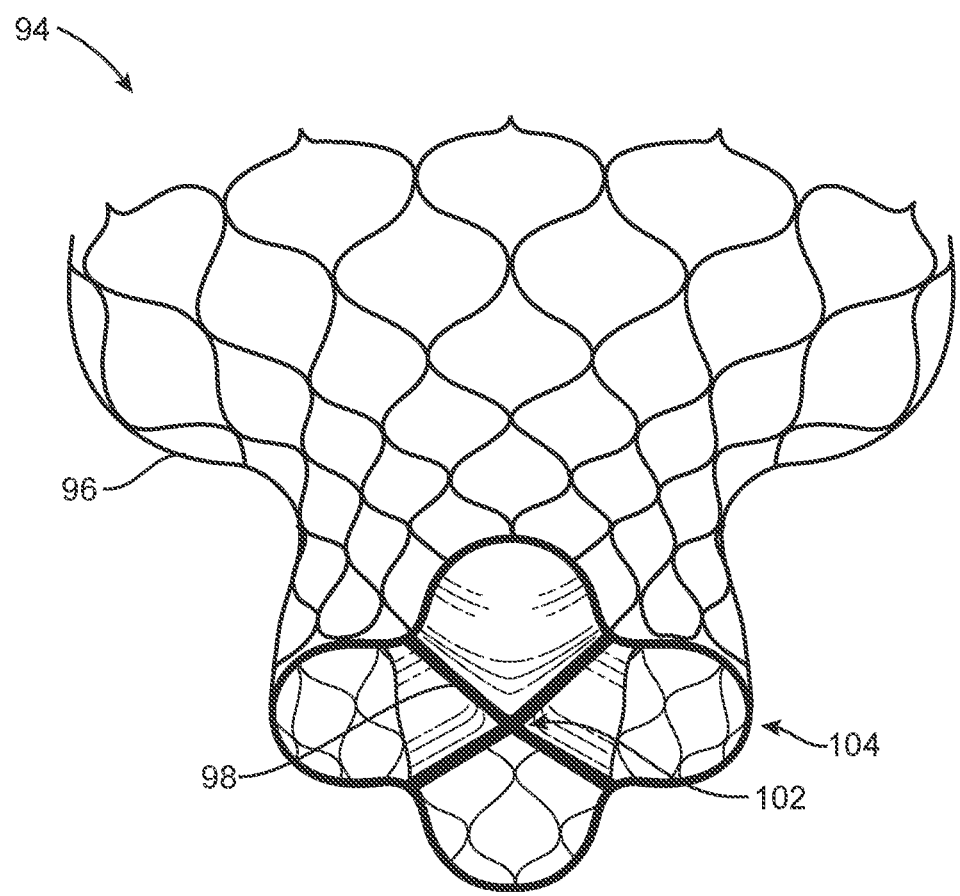

FIG. 11 illustrates a bottom-front perspective view of the valve prosthesis of FIG. 10 in a closed position.

Figure 12:
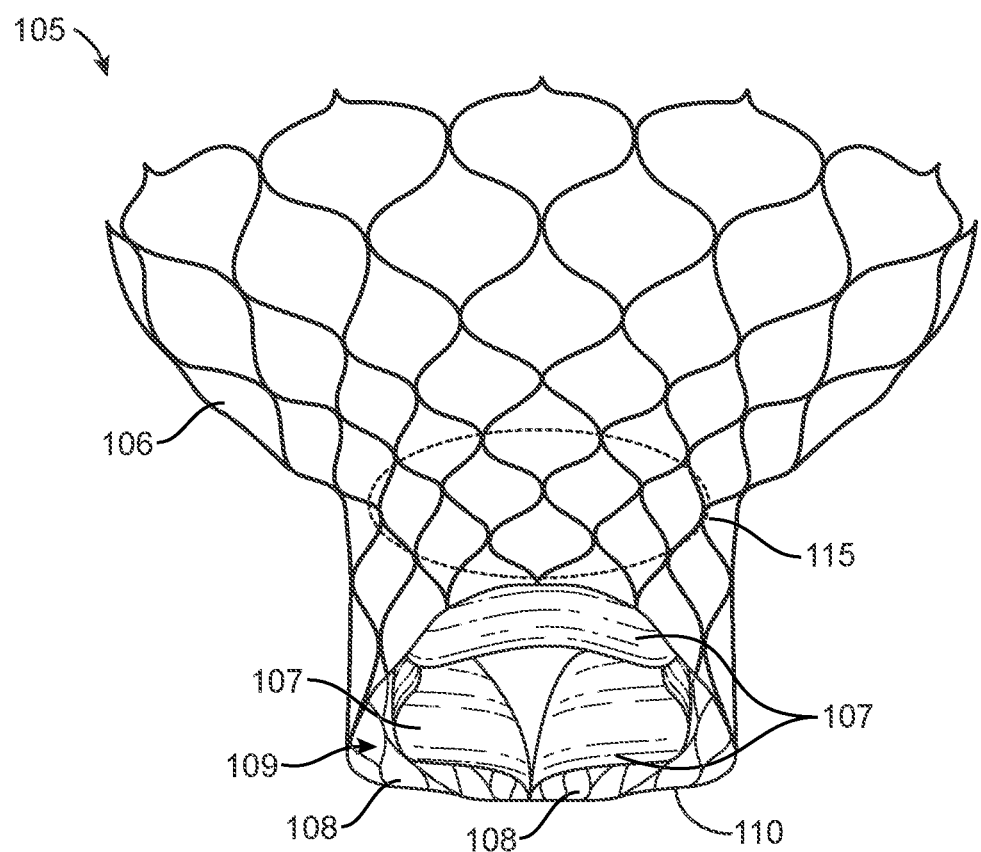

FIG. 12 illustrates a bottom-front perspective view of a valve prosthesis in an open position in accordance with an embodiment.

Figure 13:
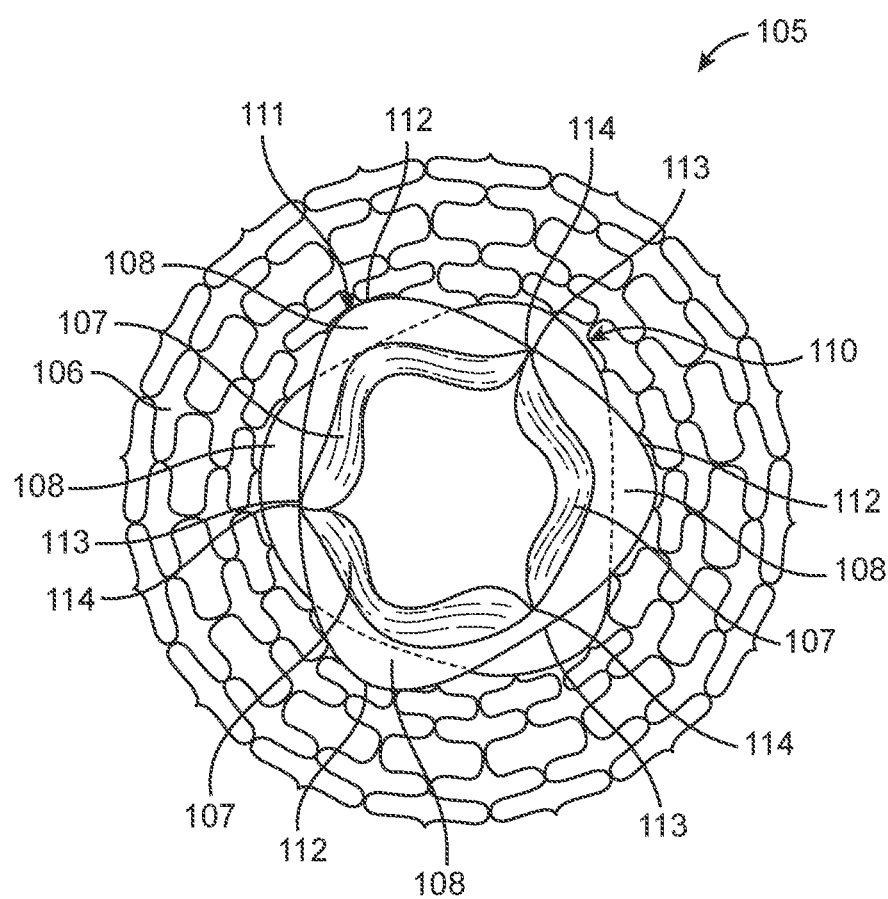

FIG. 13 illustrates a bottom view of the valve prosthesis of FIG. 12.

Figure 14:
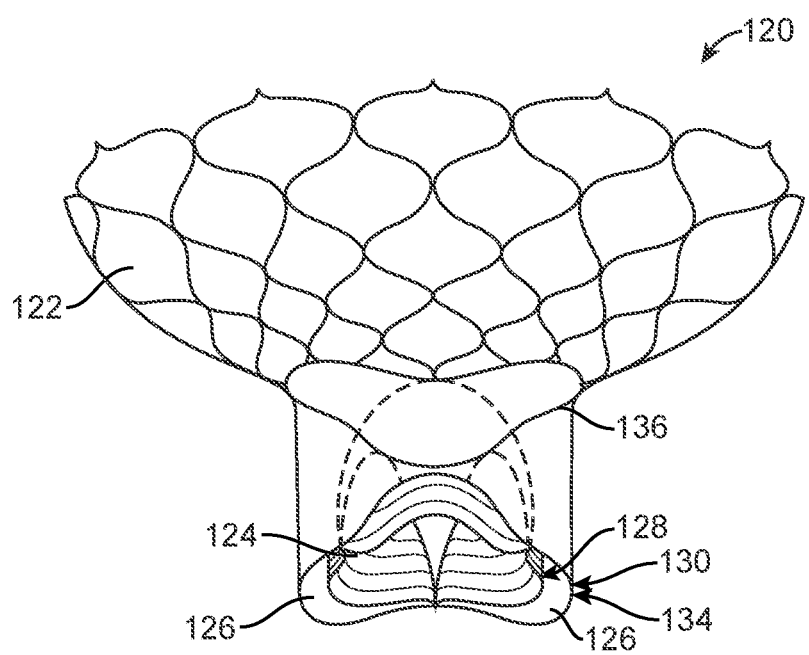

FIG. 14 illustrates a bottom-front perspective view of a valve prosthesis in an open position in accordance with an embodiment.

Figure 15:
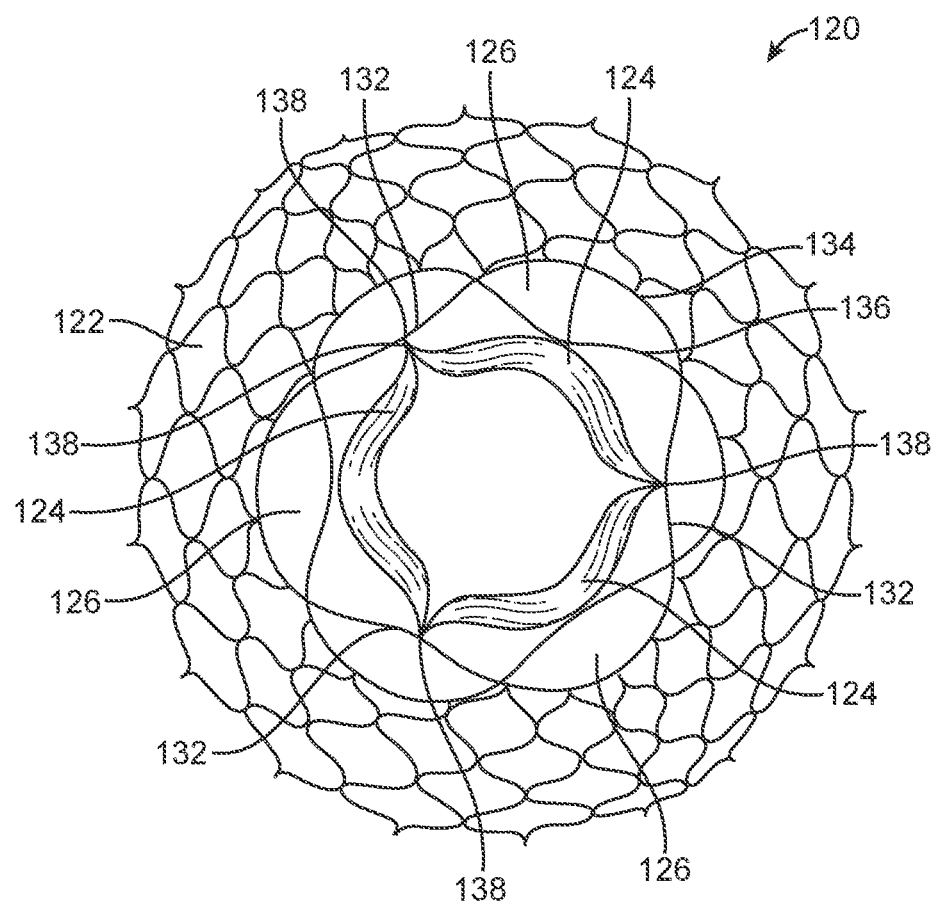

FIG. 15 illustrates a bottom view of the valve prosthesis of FIG. 14.

FIG. 16a illustrates a frame in accordance with an embodiment.

FIG. 16b illustrates a saddle shape formed when the frame of FIG. 16a is expanded.

Figure 17:
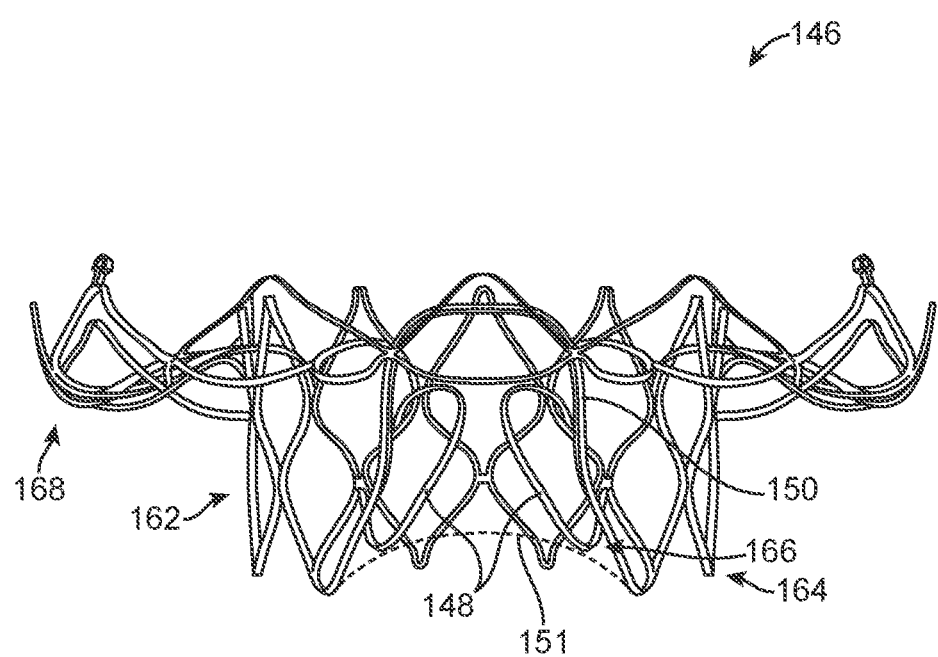

FIG. 17 illustrates a front view of a frame in accordance with an embodiment.

Figure 18:
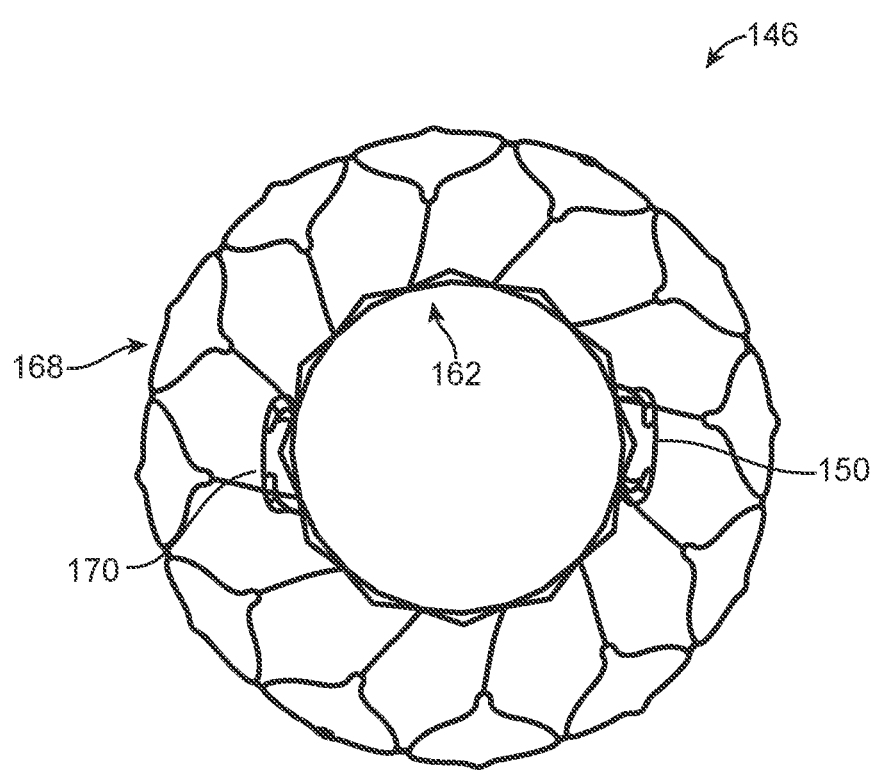

FIG. 18 illustrates a top view of the frame of FIG. 17.

Figure 19:
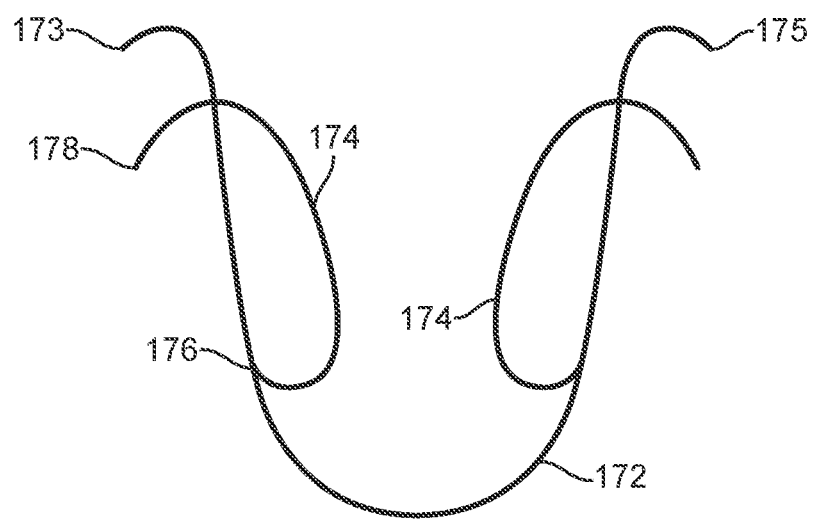

FIG. 19 illustrates a simplified drawing of a portion of a frame in accordance with an embodiment.

DETAILED DESCRIPTION

The following detailed description refers to the accompanying figures which illustrate several embodiments. Other embodiments are possible. Modifications can be made to the embodiments described herein without departing from the spirit and scope of the present invention. Therefore, the following detailed description is not meant to be limiting.

Figure 1:
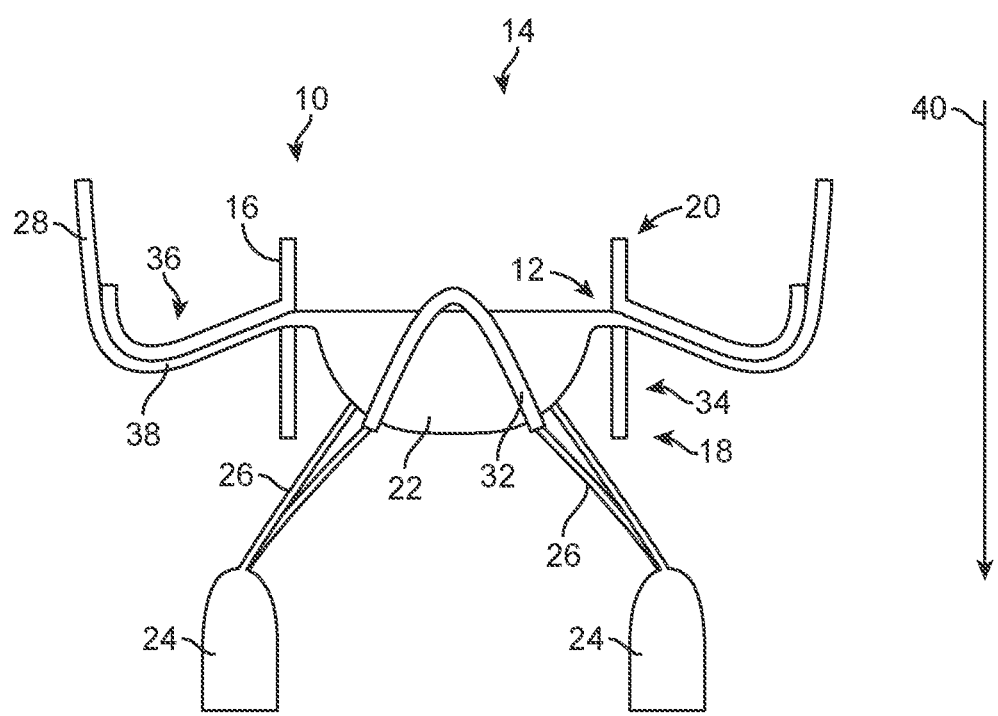
FIG. 1 illustrates a front view of a simplified drawing of a heart valve prosthesis in accordance with an embodiment implanted within a mitral valve annulus.

FIG. 1 illustrates a front view of a simplified drawing of a heart valve prosthesis 10 implanted within a mitral valve annulus 12 of a mitral valve site 14. Valve prosthesis 10 can be configured to be implanted in annulus 12 to replace the function of a native heart valve, such as the aortic, mitral, pulmonary, or tricuspid heart valve. In some embodiments, a single valve prosthesis 10 can be designed for use with multiple heart valves.

Heart valve prosthesis 10 includes a frame 16 that supports a prosthetic valve body (not shown). The valve body can be formed, for example, from one or more biocompatible synthetic materials, synthetic polymers, autograft tissue, homograft tissue, xenograft tissue, or one or more other suitable materials. In some embodiments, the valve body can be formed, for example, from bovine, porcine, equine, ovine, and/or other suitable animal tissues. In some embodiments, the valve body can be formed, for example, from heart valve tissue, pericardium, and/or other suitable tissue. In some embodiments, the valve body can comprise one or more valve leaflets. For example, the valve body can be in the form of a tri-leaflet bovine pericardium valve, a bi-leaflet valve, or another suitable valve. In some embodiments, the valve body can comprise three leaflets that are fastened together at enlarged lateral end regions to form commissural joints, with the unattached edges forming coaptation edges of the valve body. The leaflets can be fastened to a skirt, which in turn can be attached to the frame. The upper ends of the commissure points can define an outflow portion corresponding to an outflow end 18 of valve prosthesis 10. The opposite end of the valve can define an inflow or distal portion corresponding to an inflow end 20 of valve prosthesis 10. As used herein the terms "distal" or "outflow" are understood to mean downstream to the direction of blood flow. The terms "proximal" or "inflow" are understood to mean upstream to the direction of blood flow.

In some embodiments, frame 16 itself can be formed entirely or in part by a biocompatible material. In some embodiments, one or more portions of frame 16 can be self-expandable and/or balloon expandable. For example, one or more portions of frame 16 can be formed from a shape memory alloy, such as certain nitinol (nickel titanium) alloys that can, for example, exhibit shape memory and/or superelasticity.

The actual shape and configuration of valve prosthesis 10 can depend upon the valve being replaced. For example, with respect to mitral valves, during a conventional human cardiac cycle, the fibrous skeleton, anterior and posterior leaflets 22, papillary muscles 24, chordae tendinea 26, atrial wall 28, outflow tract 30, and ventricular wall (not shown) can all interplay to render a competent valve. For example, the complex interaction between the leaflets 22, papillary muscles 24, and chordae 26 can help maintain the continuity between the atrio-ventricular ring and the ventricular muscle mass, which can help provide for normal functioning of the mitral valve.

In some embodiments, frame 16 can include a support arm 32 extending from a central portion 34 of frame 16 and configured to extend over and secure leaflet 22. In particular, upon implantation, support arm 32 can be configured to clamp and immobilize a corresponding leaflet 22, and hold leaflet 22 close to central portion 34. In some embodiments, frame 16 can include multiple support arms 32 with each support arm 32 corresponding to a separate native leaflet 22.

In some embodiments, proper seating of valve prosthesis 10 within annulus 12 can be achieved by capturing one or more native leaflets 22 with support arms 32. Radial force generated by valve prosthesis 10 in the atrium against support arms 32 can create a "sandwich effect," which in some embodiments can seat valve prosthesis 10 by pinching leaflets 22 and atrial tissue against central portion 34.

In some embodiments, support arm 32 can be coated and/or covered with a biocompatible polymer, such as, for example, expanded polytetrafluoroethylene (ePTFE). In some embodiments, a covering can be a biocompatible fabric or other biocompatible material, such as bovine or porcine pericardium tissue.

In some embodiments, support arm 32 can be sized or shaped to tension chordae 26. Chordae 26 can connect to leaflets 22 and can act like "tie rods" in an engineering sense. In some patients, not only can chordae 26 help prevent prolapse of the native leaflets 22 during systole, they can also help support the left ventricular muscle mass throughout the cardiac cycle. In some embodiments, the tension between chordae 26 and leaflets 22 can serve to prevent frame 16 from lifting into the patient's atrium. In some embodiments, chordae tension can serve to substantially prevent paravalvular leakage. In some embodiments, paravalvular leakage can be substantially prevented by positioning a sealing surface of the valve between inflow end 20 and outflow end 18.

In some embodiments, support arms 32 can be sized or shaped to increase valve stability. Support arm 32 can, for example, serve to substantially prevent leaflets 22 from obstructing flow through outflow tract 30. In some embodiments, support arms 32 can serve to prevent leaflets 22 from interacting with prosthetic leaflets of valve prosthesis 10. In some embodiments, support arm 32 can position leaflet 22 to minimizing perivalvular leaks and/or maintain proper alignment of the valve prosthesis. In some embodiments, support arm 32 can serve to avoid systolic anterior mobility and/or maintain valve stability by preventing migration of the valve into the atrium or ventricle. In some embodiments, support arm 32 can be configured to enhance overall frame strength.

In some embodiments, frame 16 can include an inlet portion 36 configured to engage floor 38 of the outflow tract of the native heart atrium. In some embodiments, inlet portion 36 can restrict movement of valve prosthesis 10 in a downstream direction 40 of blood flow at valve site 14.

In some embodiments, inlet portion 36 is configured to deform floor 38 of the outflow tract in an upstream direction of blood flow at the valve site. For example, the radial force of central portion 34 on annulus 12 can lift floor 38 in an upstream direction to follow the curvature of inlet portion 36. In some embodiments, inlet portion 36 can be configured such lifted annulus 12 causes chordae 26 to be stretched without rupturing. In some embodiments, inlet portion 36 can be sized to contact the entirety of floor 38 and a portion of atrial wall 28. One example of such a configuration is shown in FIG. 1. In some embodiments, inlet portion 36 is sized to contact a substantial majority of floor 38. Other suitable configurations can be used. In some embodiments, frame 16 can be smaller than annulus 12. In some embodiments, such a configuration can serve to prevent radial force on frame 16 from annulus 12, which can serve to maintain a desired shape of a prosthetic valve supported within frame 16.

Because valve prosthesis 10 can be used in a portion of the body that undergoes substantial movement, it can be desirable for one or more portions of valve prosthesis 10, such as frame 16 to be flexible. For example, in some embodiments, at least a portion of inlet portion 36 can have a flexibility from about 0.8 N/m to about 2 N/m. In some embodiments, at least a portion of inlet portion 36 can have a flexibility of about 1.25 N/m. In some embodiments, inlet portion 36 can include one or more diamond-shaped cells. In some embodiments, inlet portion 36 can be formed of twisted strands of nitinol.

Central portion 34 of frame 16, which can be configured to conform to annulus 12. In some embodiments, such a configuration can help anchor valve prosthesis 10 within annulus 12 to prevent lateral movement or migration of valve prosthesis 10 due to the normal movement during the cardiac cycle of the heart.

Central portion 34 can be shaped to adapt to the specific anatomy of an individual. For example, in some embodiments, central portion 34 is configured to flex and deform so as to mimic a natural cardiac movement of the heart through the cardiac cycle. In some embodiments, central portion 34 is substantially rigid to avoid flexing or deformation during the cardiac cycle.

The shape of central portion 34 can be configured to reduce the risk of valve prosthesis migration and perivalvular leakage. In some embodiments, central portion 34 can define a substantially circular, oval, elliptical, saddle-shaped, or non-geometric shape. In some embodiments, central portion 34 can be formed to have a substantially straight profile (for example, being substantially cylindrical and parallel to a longitudinal axis of frame 16). Central portion 34 can have one or more flared portions (for example, diverging away from a longitudinal axis of frame 16).

In some embodiments, central portion 34 can be wider than the native valve at annulus 12. In some embodiments, such a configuration can reduce the likelihood of migration of valve prosthesis 10 into the ventricle. In some embodiments, such a configuration can improve sealing of valve prosthesis 10 against atrial wall 28. In some embodiments, frame 16 is designed to provide axial fixation by creating tension in the chordae 26, which can hold inlet portion 36 of frame 16 against annulus 12. A transition zone between an inflow portion and an outflow portion of frame 16 can provide sealing with the anatomy to prevent paravalvular leakage of frame 16. In some embodiments, frame 16 is shaped and sized so as to anchor frame 16 within annulus 12 by itself or in combination with chordae 26.

Figure 2:
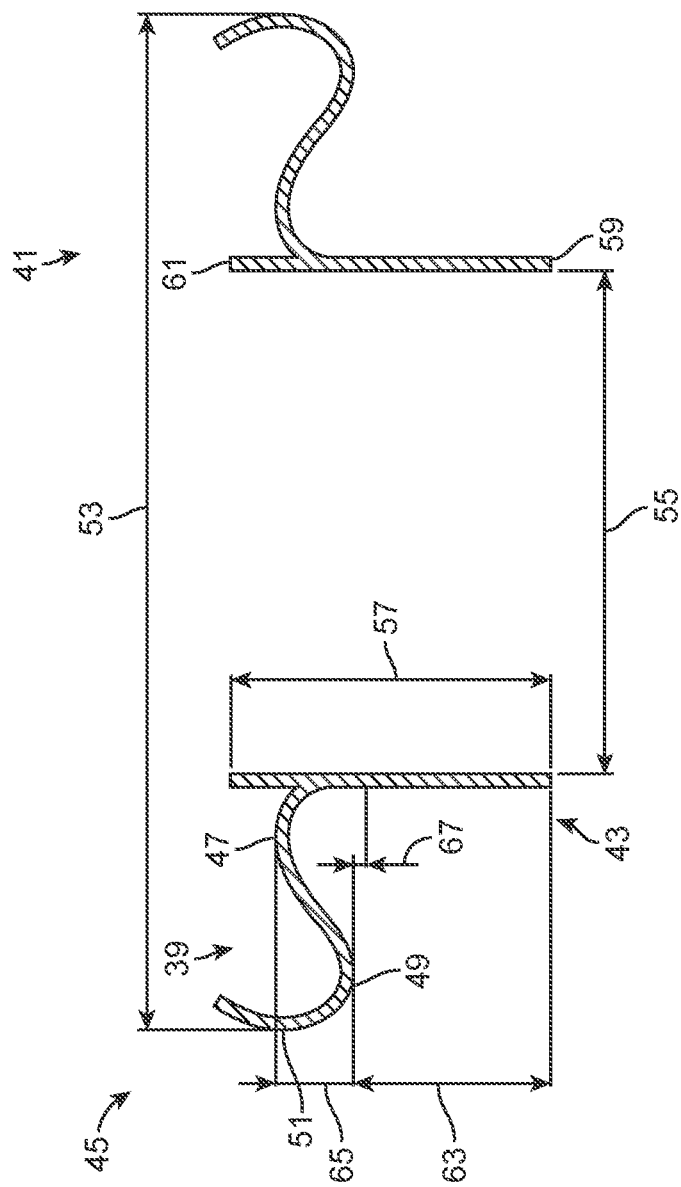
FIG. 2 illustrates a cross-sectional view of a frame in accordance with an embodiment.

FIG. 2 illustrates a cross-sectional view of a frame 41 in accordance with an embodiment. Frame 41 can include a central portion 43 attached to an inlet portion 45. In some embodiments, inlet portion 45 can be substantially S-shaped. For example, inlet portion 45 can include one or more curves, such as curves 47, 49, and 51, which together can approximate an S-shape. For example, in some embodiments, inlet portion 45 includes extension 39 that protrudes in a radially outward direction from central portion 43 of frame 41. The substantial "S" shape of inlet portion 45 can be formed by extension 39 bending in a first curve 47 from inflow end 61 towards outflow end 59, and then bending in a second curve 49 back towards inflow end 61. One embodiment of such an S-shape is shown for example in FIG. 2. In some embodiments, extension 39 can additionally bend in a third curve 51 towards a radially inward direction.

In some embodiments, frame 41 can include an outer diameter 53 of approximately 60.37 mm, a valve diameter 55 of approximately 30.42 mm, a valve height 57 between an outflow end 59 of frame 41 and an inflow end 61 of frame 41 of approximately 16.97 mm, an effective valve height 63 between an outflow end 59 of frame 41 and curve 49 of approximately 10.56 mm, an upper s-shape dimension 65 between curve 47 and 49 of approximately 3.14 mm, and a lower s-shape dimension 67 between curve 49 and the first full node of the valve section from inflow end 61 of approximately 2.51 mm.

In some embodiments, inlet portion 45 can be configured to contact a patient's atrial anatomy at a lower point on frame 41 compared to conventional frame designs. In some embodiments, such a configuration can serve to increase chordal tension. In some embodiments, the shape and size of inlet portion 45 can be configured to conform to the shape of the native mitral annulus and left atrium. In some embodiments, such a configuration can result in varying degrees of deformation (e.g., a flattening) of inlet portion 45, which can serve to create an excellent seal between inlet portion 45 and the native anatomy. In some embodiments, one or more of the above configurations can serve to reduce paravalvular leakage compared to other frame designs.

Inlet portion 45 can be configured to maintain contact throughout a patient's cardiac cycle. In some embodiments, changes in chordal tension can be accommodated by partially flattening inlet portion 45. In some embodiments, the flattening of inlet portion 45 can hold a spring load. In some embodiments, as changes in the chordal tension throughout the cardiac cycle occur, the spring load can serve to maintain contact and sealing with the tissue despite the changing tension.

FIGS. 3, 4a and 4b illustrate a frame 42. FIG. 3 illustrates a front view of frame 42. FIG. 4a illustrates a view of frame 42 implanted in a native mitral valve site 44 and FIG. 4b illustrates an enlarged view of a portion of FIG. 4a. Valve site 44 includes an annulus 46, native leaflets 48, chordae 50, and papillary muscles 52.

Figure 4:
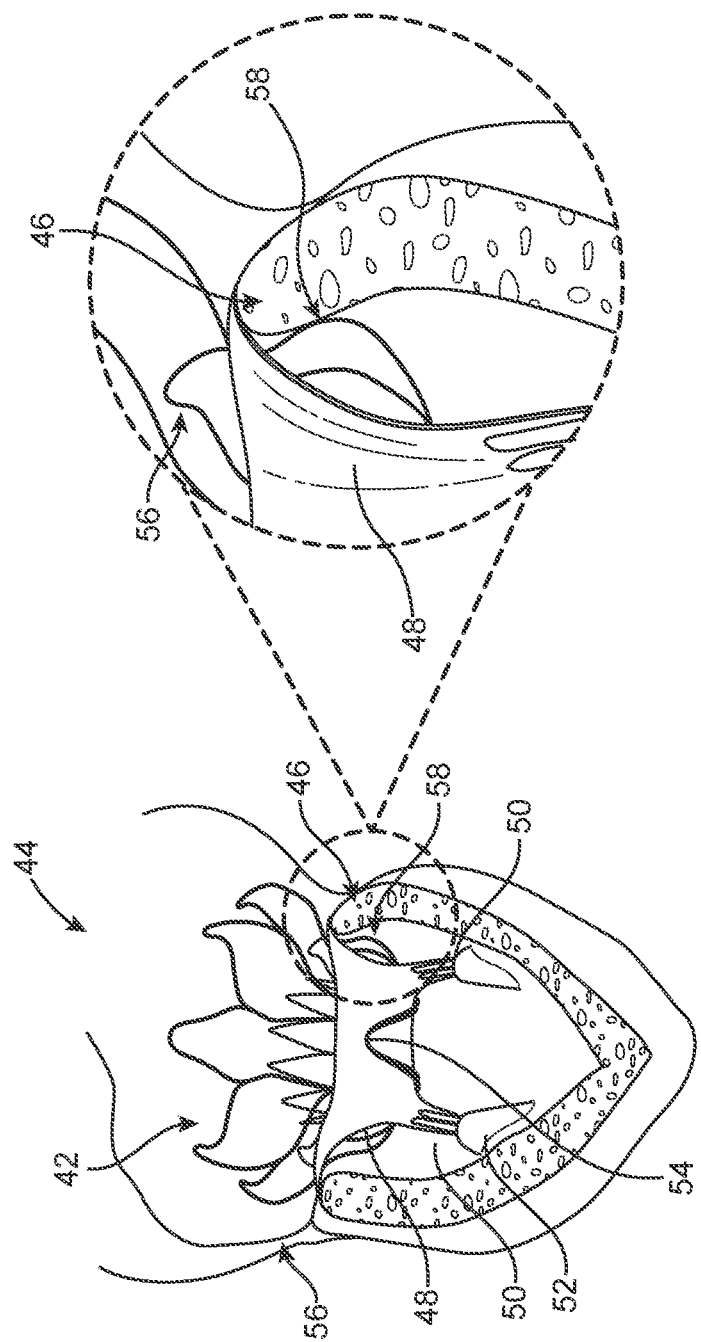

Frame 42 includes support arms 54, inlet portion 56, and a central portion 58. A partially hourglass-shaped central portion 58 of frame 42 is configured to pinch a muscular ridge of annulus 46 to provide axial fixation of frame 42 within valve site 44. The hourglass shape portion of frame 42 can be located on central portion 58 corresponding to the location of the commissures of the native valve within the valve site. One example of such a configuration is shown in FIGS. 3-4. Other suitable configurations can be used. In some embodiments, a portion of central portion 58 is angled about 90 degrees from the angle of support arms 54. Frame 42 can also provide axial fixation by creating chordal tension of chordae 50.

FIGS. 5-6 illustrate a valve prosthesis 60. FIG. 5 illustrates a front view of a valve prosthesis 60. FIG. 6 illustrates a top view of valve prosthesis 60. Valve prosthesis 60 includes a valve body 62 supported within a frame 64. Frame 64 includes an inlet portion 66, an hourglass shaped central portion 68 and support arms 70. Support arms 70 can be configured to capture leaflets during delivery of prosthesis 60. Central portion 68 can pinch a muscular ridge of the native annulus. The hourglass shape of frame 64 can be located on central portion 68 around the entire circumference of frame 64. One example of such a configuration is shown in FIGS. 5-6. Other suitable configurations can be used. Frame 64 can also provide axial fixation by creating chordal tension of chordae.

FIGS. 7, 8, and 9a-9b illustrate a frame 72. FIG. 7 illustrates a front view of a frame 72. FIG. 8 illustrates a top view of a valve prosthesis 74 including a valve body 76 supported by frame 72. FIG. 9a illustrates a view of valve prosthesis 74 implanted in a native valve site 78. FIG. 9b is an enlarged view of a portion of FIG. 9a. Valve site 78 includes annulus 80, chordae 82, and papillary muscles 84.

Frame 72 includes an inlet portion 86, an hourglass shaped central portion 88 and support arms 90. Support arms 90 are configured to capture leaflets during device delivery. Axial fixation of frame 72 can be achieved through the hourglass shaped central portion 88 pinching a muscular ridge of the native annulus. Frame 72 can have an elliptical outflow end 92. The larger diameter of the ellipse can be positioned near the mitral valve commissures of the native valve. The shorter part of the ellipse can be near the aorto-mitral fibrous continuity of the native valve. Although outflow end 92 can be elliptical, valve body 76 of frame 72 can remain cylindrical. One example of such a configuration is shown in FIGS. 7-9. Other suitable configurations can be used. Frame 72 can also provide axial fixation by creating chordal tension of chordae 82.

FIGS. 10-11 illustrate a valve prosthesis 94. FIG. 10 illustrates bottom-front perspective view of valve prosthesis 94 in an open position. FIG. 11 illustrates a bottom-front view of valve prosthesis 94 in a closed position. Valve prosthesis 94 includes a frame 96 along with a valve body including prosthetic leaflets 98. An outflow end 104 of frame 96 flares outwardly to allow for gaps 100 between an outflow end 102 of leaflets 98 and outflow end 104 of frame 96.

FIGS. 12-13 illustrate a valve prosthesis 105. FIG. 12 illustrates a bottom-front view of valve prosthesis 105 in an open position. FIG. 13 illustrates a bottom view of valve prosthesis 105. Valve prosthesis 105 includes a frame 106 along with a valve body including prosthetic leaflets 107. As shown, for example in FIG. 13, a cross-section of a valve outlet 111 is a rounded triangle with each vertex 112 of the triangle aligned with a corresponding leaflet 107 of the valve body to provide gaps 108 between an outflow end 110 of frame 106 and the outflow end 109 of leaflet 107 when leaflet 107 is fully open. In some embodiments, the midsection of sides 113 of frame 106 are aligned with corresponding commissures 114 of the valve body.

The cross-section of a valve base 115 can be a rounded triangular and rotated about 60 degrees relative to the cross-section of valve outlet 111 so that the body forms a roughly cylindrical shape. One example of such a configuration is shown in FIG. 13. Other suitable configurations can be used.

FIGS. 14-15 illustrate a valve prosthesis 120. FIG. 14 illustrates valve prosthesis 10 in an open position. FIG. 15 illustrates a bottom view of valve prosthesis 120. Valve prosthesis 120 includes a frame 122 along with a valve body including prosthetic leaflets 124. Frame 122 is configured to allow for gaps 126 between an outflow end 128 of leaflets 124 and an outflow end 130 of frame 122 when leaflets 124 are fully open. In some embodiments, gaps 126 can be sized and shaped to minimize or eliminate contact between leaflets 124 and frame 122. In some embodiments, gaps 126 can be up to 5 millimeters wide. In some embodiments, gaps 126 can be larger than 5 millimeters. In some embodiments, the mid-section of sides 132 are aligned with corresponding commissures 138 of the valve body.

Sides 132 of the rounded triangle of valve outlet 134 curve inward. The overall shape of the cross-section of valve outlet 134 can be described as clover-leaf shaped. In addition, sides 132 of the rounded triangle of valve base 136 curve inward and can also be described as clover-leaf shaped. The cross-section of valve base 136 can be rotated about 60 degrees relative to the cross-section of valve outlet 134 so that the valve forms a roughly cylindrical shape. In some embodiments, valve base 136 can be substantially cylindrical and valve outlet 134 can flare out from valve base 136. In some embodiments, leaflets 124 can be attached at valve base 136. Other suitable configurations can be used.

FIG. 16a illustrates a frame 140. A non-planar shape of one or more of the various frames described herein can be achieved by changing the location of nodes formed within the frame. For example, a laser cut pattern of a frame can be modified, along with new fixtures for heat seating to achieve such a configuration. In particular, frame 140 includes nodes 142 arranged in a sinusoidal pattern. In some embodiments, such a configuration can have the effect of changing the shape of frame 140 when frame 140 is expanded. The sinusoidal pattern of nodes 142 within frame 140 can, for example, result in a three dimensional saddle shape 144 of frame 140, shown for example in FIG. 16b, that can mimic the native anatomy at a mitral annulus. In some embodiments, frame 140 can include a modified inflow section 143 and an unmodified valve section 145.

FIGS. 17-18 illustrate a frame 146 for a valve prosthesis. FIG. 17 illustrates a front view of frame 146. FIG. 18 illustrates a top view of frame 146. Frame 146 includes central portion 162, inlet portion 168, and chordae guiding element 148. Chordae guiding element 148 extends from support arm 150 and is configured to engage chordae of the native valve site. As described above, chordae can connect to native leaflets and act like "tie rods" in an engineering sense. Not only can the chordae help prevent prolapse of the native leaflets during systole, they can also help support the left ventricular muscle mass throughout the cardiac cycle. In some embodiments, it can be desirable to impart tension onto the chordae with support arms, such as support arms 150. However, excessive tension can cause the chordae to rupture which can reduce the effectiveness of valve prosthesis 156. In some embodiments, the shape and location of support arms 150 on frame 146 can reduce tension imparted onto the chordae by support arms 150.

In some embodiments, chordae guiding element 148 can be formed by a rigid wire material and can be shaped to avoid hard angles and/or sharp edges. In some embodiments, chordae guiding element 148 can be the same thickness and material as support arm 150. In some embodiments, chordae guiding element 148 can be bent in the shape of a semicircle, oval, lobe, or other suitable shape. Chordae guiding element 148 can be configured to angle chordae 152 so that the chordae are stretched to restrict movement of valve prosthesis 156 in a downstream direction of blood flow at valve site 154.

In some embodiments, chordae guiding element 148 can be configured to interact with one or more native leaflets instead of the chordae. In some embodiments, one or more of the above configurations can be used in combination with other coatings, coverings, or configurations to reduce chordal abrasion or rupture. In some embodiments, the corners of one or both of support arm 150 and chordae guiding elements 148 can be rounded, which in some embodiments can avoid sharp corners that can cause chordal abrasion or rupture.

In some embodiments, chordae guiding element 148 is positioned such that chordae 152 are stretched to prevent movement of valve prosthesis 156 relative to the native valve over the course of the cardiac cycle, without rupturing chordae 152. In some embodiments, such a configuration can provide added stability to valve prosthesis 156 while preventing damage to chordae 152.

In some embodiments, chordae guiding element 148 can be directly attached to support arm 150 and can extend outward from the leaflet securing arm. A first end and a second end of chordae guiding element 148 can be attached to a central portion 162 of frame 146. In some embodiments, one end of chordae guiding element 148 can be directly attached to support arm 150 and a second end of chordae guiding element 148 can be directly attached to central portion 162. In some embodiments, chordae guiding element 148 can reduce bending of the native chordae by redistributing the force applied by support arm 150 to chordae 152.

In some embodiments, an outflow end 164 of support arm 150 is longitudinally offset from an outflow end 166 of chordae guiding element 148 by a distance to reduce the bending of chordae 152. The longitudinal offset can, for example, be from about 1 mm to about 5 mm in the longitudinal direction.

In some embodiments, outflow end 164 of support arm 150 is laterally offset from outflow end 166 of chordae guiding element 148 by a distance to reduce the bending of chordae 152. The lateral offset can, for example, be from about 1 mm to about 5 mm in the lateral direction.

In some embodiments, chordae guiding element 148 can be configured to create a tapered entry for chordae. In some embodiments, a longitudinal and/or lateral offset between support arms 150 and chordae guiding element 148 can be configured to guide chordae substantially along a portion of an arc, such as along a portion of parabolic arc 151 (shown in broken lines) in FIG. 17. In some embodiments, arc 151 can be circular rather than parabolic, stepped, or another desired shape. In some embodiments, arc 151 can guide chordae exiting support arm 150 and chordae guiding element 148 to approximate a native anatomical angle. In some embodiments, such a configuration can reduce abrasion of the chordae and/or maintain a desired chordal tension. In some embodiments, a desired chordal tension is sufficient to prevent frame 146 from lifting into the atrium. In some embodiments, a desired chordal tension is sufficient to substantially prevent frame 146 from moving and/or rocking during the cardiac cycle.

In some embodiments, the angle formed by arc 151 can serve to decrease an angle of entry of the chordae into support arm 150, which can reduce chordal abrasion forces acting on the chordae from frame 146. In some embodiments, support arms 150 and chordae guiding element 148 are configured to substantially eliminate bending of the chordae. In some embodiments, support arms 150 and chordae guiding element 148 are configured to bend the chordae less than approximately 90 degrees. In some embodiments, chordae are guided solely by chordae guiding element 148 and are guided by chordae guiding element so as not to touch support arms 150. In some embodiments, a second support arm 170 can connect to and extend from central portion 162 and can be configured to extend over and engage a second native leaflet of the native valve. A second chordae guiding element can also be connected to second support arm 170 and can be configured similarly to first support arm 150.

FIG. 19 illustrates a simplified drawing of a support arm 172. Support arm 172 can include a first end 173 and a second end 175. One or both of first end 173 and second end 175 can be connected to the same or different portions of the frame (not shown). Support arm 172 includes a first and second chordae guiding element 174, which can function similarly to the chordae guiding elements described above. Each chordae guiding element 174 can include a first end 176 attached to support arm 172 and a second end 178 attached to the frame. In some embodiments, first end 176 can be connected to the frame. In some embodiments, both first end 176 and second end 178 can be connected to support arm 172.

One or more of the valve prostheses described herein can be implanted into an annulus of a native cardiac valve through a suitable delivery method. For example, the valve prosthesis can be implanted through conventional open-heart surgery techniques. In some embodiments, the valve prosthesis can be delivered percutaneously. For example, in some percutaneous techniques, valve prosthesis can be compacted and loaded onto a delivery device for advancement through a patient's vasculature. The valve prosthesis can be delivered through an artery or vein, a femoral artery, a femoral vein, a jugular vein, a subclavian artery, an axillary artery, an aorta, an atrium, and/or a ventricle. The valve prosthesis may be delivered via a transfemoral, transapical, transseptal, transatrial, transventrical, or transaortic procedure.

In some embodiments, the valve prosthesis can be delivered transfemorally. In such a delivery, the delivery device and the valve prosthesis can be advanced in a retrograde manner through the femoral artery and into the patient's descending aorta. A catheter can then be advanced under fluoroscopic guidance over the aortic arch, through the ascending aorta, into the left ventricle, and mid-way across the defective mitral valve. Once positioning of the catheter is confirmed, the delivery device can deploy the valve prosthesis within the annulus. The valve prosthesis can then expand against and align the prosthesis within the annulus. In some embodiments, as the valve prosthesis is expanded, it can trap leaflets against the annulus, which can retain the native valve in a permanently open state.

In some embodiments, the valve prosthesis can be delivered via a transapical procedure. In a transapical procedure, a trocar or overtube can be inserted into a patient's left ventricle through an incision created in the apex of the patient's heart. A dilator can be used to aid in the insertion of the trocar. In this approach, the native valve (for example, the mitral valve) can be approached from the downstream relative to the blood flow. The trocar can be retracted sufficiently to release the self-expanding valve prosthesis. The dilator can be presented between the leaflets. The trocar can be rotated and adjusted to align the valve prosthesis in a desired alignment. The dilator can be advanced into the left atrium to begin disengaging the proximal section of the valve prosthesis from the dilator.

In some embodiments, the valve prosthesis can be delivered via a transatrial procedure. In such a procedure, a dilator and trocar can be inserted through an incision made in the wall of the left atrium of the heart. The dilator and trocar can then be advanced through the native valve and into the left ventricle of heart. The dilator can then be withdrawn from the trocar. A guide wire can be advanced through the trocar to the point where the valve prosthesis comes to the end of the trocar. The valve prosthesis can be advanced sufficiently to release the self-expanding frame from the trocar. The trocar can be rotated and adjusted to align the valve prosthesis in a desired alignment. The trocar can be withdrawn completely from the heart such that the valve prosthesis self-expands into position and can assume the function of the native valve.

The choice of materials for the various valve prostheses described herein can be informed by the requirements of mechanical properties, temperature sensitivity, biocompatibility, moldability properties, or other factors apparent to a person having ordinary skill in the art. For example, one more of the parts (or a portion of one of the parts) can be made from suitable plastics, such as a suitable thermoplastic, suitable metals, and/or other suitable materials.

The foregoing description of the invention has been presented for purposes of illustration and description. It is not intended to be exhaustive or to limit the invention to the precise form disclosed. Other modifications and variations can be possible in light of the above teachings. The embodiments and examples were chosen and described in order to best explain the principles of the invention and its practical application and to thereby enable others skilled in the art to best utilize the invention in various embodiments with modifications as are suited to the particular use contemplated. It is intended that the appended claims be construed to include other alternative embodiments of the invention.

The invention claimed is:

1. A valve prosthesis comprising:
   a frame including
      a central portion,
      a support member extending from the central portion, the support member including a leaflet engagement portion configured to engage a native valve leaflet and a chordae engagement portion configured to engage and tension at least one native chorda to thereby restrict movement of the valve prosthesis in an upstream direction of blood flow, wherein an outflow end of the leaflet engagement portion is laterally offset from an outflow end of the chordae engagement portion, and
      an inlet portion extending radially outward from the central portion and configured to engage a floor of an outflow tract of a native heart atrium to thereby restrict movement of the valve prosthesis in a downstream direction of blood flow; and
   a prosthetic valve secured to the central portion.

2. The valve prosthesis of claim 1, wherein the support member and the inlet portion act in opposition to create a seal between the inlet portion and a floor of an outflow tract of a native heart atrium after implantation of the valve prosthesis.

3. The valve prosthesis of claim 2, wherein the seal is maintained throughout a cardiac cycle of a patient.

4. The valve prosthesis of claim 2, wherein the seal is maintained during changes in chordal tension throughout a cardiac cycle of a patient.

5. The valve prosthesis of claim 1, wherein at least a portion of the inlet portion has a flexibility of between 0.8 N/m to 2 N/m.

6. The valve prosthesis of claim 1, wherein a cross-section of the inlet portion is substantially s-shaped.

7. The valve prosthesis of claim 1, wherein at least a portion of the frame is self-expandable.

8. The valve prosthesis of claim 1, wherein at least a portion of the frame is balloon-expandable.

9. The valve prosthesis of claim 1, wherein the support member of the frame comprises multiple support members.

10. The valve prosthesis of claim 9, wherein each support member comprises at least one engagement portion configured to engage and tension at least one native chorda to thereby restrict movement of the valve prosthesis in an upstream direction of blood flow.

11. The valve prosthesis of claim 1, wherein the inlet portion is configured to deform a floor of an outflow tract of a native heart atrium.

12. The valve prosthesis of claim 1, wherein the inlet portion is configured to engage an atrial wall.

13. The valve prosthesis of claim 1, wherein the central portion is configured to conform to a native annulus.

14. The valve prosthesis of claim 1, wherein the central portion has an hourglass-shape.

15. The valve prosthesis of claim 1, wherein the chordae engagement portion is configured to angle the at least one native chorda so that the at least one native chorda is stretched.

16. The valve prosthesis of claim 1, wherein the leaflet engagement portion is a support arm having a first end directly attached to the central portion and a second end directly attached to the central portion.

17. The valve prosthesis of claim 16, wherein the chordae engagement portion has a first end directly attached to the support arm and a second end directly attached to the support arm.

18. The valve prosthesis of claim 16, wherein the chordae engagement portion has a first end directly attached to the support arm and a second end directly attached to the central portion.

19. The valve prosthesis of claim 16, wherein the chordae engagement portion has a first end directly attached to the central portion and a second end directly attached to the central portion.

20. The valve prosthesis of claim 1, wherein the outflow end of the leaflet engagement portion is also longitudinally offset from the outflow end of the chordae engagement portion.

* * * * *